United States Patent
Marshall et al.

(10) Patent No.: US 6,288,311 B1
(45) Date of Patent: Sep. 11, 2001

(54) CORN HYBRID P723

(75) Inventors: Lorelei C. Marshall, Iowa City; Terry J. Foley, Williamsburg, both of IA (US)

(73) Assignee: Optimum Quality Grains, LLC, Johnston, IA (US)

(*) Notice: Subject to any disclaimer, the term of this patent is extended or adjusted under 35 U.S.C. 154(b) by 0 days.

(21) Appl. No.: 09/452,756

(22) Filed: Dec. 1, 1999

(51) Int. Cl.⁷ ............... A01H 5/00; A01H 5/10; A01H 1/04; A01H 4/00; C12N 5/04

(52) U.S. Cl. ............ 800/320.1; 800/260; 800/274; 800/275; 800/271; 800/298; 435/410; 435/412; 435/424; 435/430

(58) Field of Search .................. 800/320.1, 298, 800/260, 271, 274, 275; 435/410, 412, 424, 430

(56) References Cited

U.S. PATENT DOCUMENTS 5,675,065   10/1997   Bergquist .
5,850,031   12/1998   Bergquist .

*Primary Examiner*—Gary Benzion
*Assistant Examiner*—Melissa L. Kimball
(74) *Attorney, Agent, or Firm*—Bullwinkel Partners, Ltd.

(57) ABSTRACT

A hybrid corn line having the designation P723, produced by crossing the inbred Qx47 and the synthetic P39B. P723 imparts a high oil level in the grain of certain male sterile hybrids when used as a pollinator. P723 is characterized by good plant vigor, including seedling vigor in cold soil tests, and gives higher test weight when used in the TOPCROSS® Grain Production System than other pollinators of similar oil levels. P723 has shown excellent productivity in TC BLEND® seed products of early to medium season adaptability. This invention thus relates to the seeds, plants and plant parts of P723 and its components, to plants regenerated from tissue culture of the plants of P723, to a method of producing P723, and to a method for producing high oil grain using P723 as a pollinator.

16 Claims, No Drawings

CORN HYBRID P723

FIELD OF THE INVENTION

This invention is in the field of maize breeding. Specifically, this invention relates to a novel corn hybrid having the designation P723.

BACKGROUND OF THE INVENTION

Principles of Conventional Plant Breeding

Most of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed seed of an $F_1$ single cross hybrid. This seed is then sold to commercial grain growers who plant the seed and harvest the second generation, or $F_2$ grain, for use on farm or for commercial sale.

The production of conventional single cross hybrid seed involves controlling the direction of pollination from one inbred to the other to assure the production of predominantly hybrid (cross pollinated) seed. Typically, directed pollination is accomplished by interplanting separate rows of female corn plants with male corn plants. The female corn plants that are male sterile may be produced by genetic mechanisms which render the corn tassel or pollen nonfunctional or by detasseling the plants in the field.

The development of corn hybrids requires the development of homozygous inbred lines, the crossing of these lines, and the evaluation of the crosses. Pedigree breeding, backcross conversion and recurrent selection breeding methods are used to develop the inbred lines from breeding populations. These breeding methods combine desirable traits from two or more inbred lines or various broad-based populations into breeding pools from which new inbred lines are developed by inbreeding or random mating and selection of desired phenotypes. The new inbreds are crossed with other inbreds and the resulting hybrids are evaluated to determine which have commercial value and agronomic usefulness.

The objective of typical plant breeding is to develop a hybrid with desirable traits such as resistance to diseases and insects, herbicide tolerance, tolerance to heat and drought, reduction of time to crop maturity, and improved agronomic quality. Because many crops are harvested mechanically, uniformity of plant characteristics such as germination time, stand establishment, growth rate, and fruit/seed size are also desirable.

The problem with conventional breeding techniques is that there are several grain quality traits, such as high oil concentration, that cannot readily be obtained in a high-yielding single cross hybrid. One solution to this problem has been proposed by Bergquist et al. in U.S. Pat. Nos. 5,704,160 and 5,706,603, incorporated herein by reference. A primary aspect of this method, known as the TOPCROSS® Grain Production System, is the interplanting of a pollinator corn plant possessing the characteristics for significantly increasing oil level in the resulting grain, with a male sterile hybrid corn plant. The resulting grain possesses an oil concentration much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Critical to the success of the TOPCROSS® Grain Production System is the use of a pollinator capable of enhancing the grain quality traits of the $F_1$ grain. P723 was developed for this purpose. The present invention, when used as a pollinator, imparts high oil concentration to the resulting $F_1$ grain without significant loss of yield.

SUMMARY

According to the invention, there is provided a novel corn hybrid, designated P723, that when used to pollinate an elite male sterile hybrid grain parent, produces commercial grain exhibiting improved quality grain traits, including high oil. P723 is an early flowering hybrid, broadly adapted to the corn growing areas of the Northern and Central United States. Grain from P723 has expressed high oil, and excellent test weight.

The invention thus relates to the seeds, plants and plant parts of P723; to tissue culture comprising regenerable cells of a plant part of P723; to plants regenerated from regenerable cells of the tissue culture of P723; to corn plants having substantially all the phenotypic, genotypic and/or physiological characteristics of P723; to the method of producing P723; to grain or seed produced by crossing P723 with a different corn plant wherein the resulting progeny have one-half the nuclear genotype of P723; to seed blends of P723 and male sterile corn hybrids; to a method of producing high oil grain using P723 as a pollinator in a TC BLEND® Seed Product; and to corn plants produced or derived from P723 seed wherein the corn plants have the ability to impart high oil or other grain quality traits to the F1 grain when these P723-derivatives are used in the TOPCROSS® Grain Production System.

DEFINITIONS

In the description that follows, a number of terms are used. In order to provide a clear and consistent understanding of the specification and claims, including the scope to be given such terms, the following definitions are provided:

Combining Ability. The ability of a genetic strain, when crossed with another strain, to produce a high proportion of desirable individuals.

Endosperm. The nutritive tissue formed within the embryo sac in seed plants. It commonly arises following the fertilization of the diploid polar nucleus by one male sperm.

Express. To manifest a genetic character trait.

$F_1$: The first generation of a cross.

$F_2$. The second filial generation obtained by self-fertilization or crossing inter se of $F_1$ individuals. Subsequent generations are $F_3$, $F_4$, $F_5$, etc.

Genotype. The fundamental genetic constitution of an organism.

Grain. Mature corn kernels produced by commercial growers for purposes other than growing or reproducing the species.

Grain Parent. Male sterile, elite hybrid that comprises a large majority of the plants in the TOPCROSS® Grain Production System.

Grain Quality Trait. Any attribute of grain that is of commercial value. Such traits relate to the intermediate or final use of grain and include but are not limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Homozygous. A genetic condition existing when identical alleles reside at corresponding loci on homologous chromosomes.

Hybrid. (1) The progeny of a cross fertilization between parents belonging to different genotypes. (2) The first generation offspring of a cross between two individuals differing in one or more genes. (3) A hybrid is the result of a cross between two or more components.

Inbred or Inbred Line. A substantially homozygous individual, variety or line produced by continued inbreeding. In plant breeding a nearly homozygous line usually originates by continued self-fertilization, accompanied by selection.

Kernel. The corn caryopsis comprising a mature embryo and endosperm which are products of double fertilization.

Line. (1) A group of individuals from a common ancestry. (2) A narrowly defined group that is a variety.

Male Sterile. A condition in which pollen is substantially absent or non-functional in flowering plants.

Percent Oil. The oil concentration of a corn kernel, typically determined at 0% moisture.

Phenotype. (1) Physical or external appearance of an organism as contrasted with its genetic constitution (=genotype); (2) a group of organisms with similar physical or external makeup; (3) the observed character of an individual without reference to its genetic nature.

Pollen Grain. A microspore in flowering plants that germinates to form the male gametophyte which contains three haploid nuclei. One of these fertilizes the ovum, a second fuses with the two polar nuclei to form the triploid endosperm, and the third degenerates once double fertilization has been accomplished.

Pollinators. Male fertile corn plants used to pollinate male sterile hybrid corn plants in order to produce a Grain Quality Trait in the resulting F1 grain.

Population. In genetics, a community of individuals which share a common gene pool.

Seed. Mature corn kernels produced for the purpose of propagating the species.

Single Cross. A cross between two different genotypes, each of which may be an inbred or synthetic.

Synthetic (Population). A genetically heterogeneous collection of plants of known ancestry created by the intermating of any combination of inbreds, hybrids, varieties, populations, races or other synthetics.

Synthetic Hybrid. A hybrid in which one or more genotypes used to make the hybrid is a synthetic.

TC BLEND®. A registered trademark of E.I. du Pont de Nemours and Company for a physical mixture of two or more types of seed utilized in the TOPCROSS® Grain Production System.

Test Weight. The measure of the weight of the grain in pounds for a bushel volume.

TOPCROSS®. A registered trademark of E.I. du Pont de Nemours and Company for the TOPCROSS® Grain Production System.

Yield (Bushels/Acre). The yield of corn in bushels/acre is the number of bushels of grain at harvest per acre, where one bushel is equal to 56 pounds adjusted to 15.5% moisture.

DETAILED DESCRIPTION OF THE INVENTION

P723 is a high oil hybrid having superior agronomic characteristics and the ability to impart desirable grain quality traits to grain when used as a pollinator in the TOPCROSS® Grain Production System. P723 is adapted over a wide area of the Northern and Central regions of the U.S. corn belt. P723 can be used advantageously in TC BLEND® Seed Corn Products with grain parents from approximately 102–112 relative maturity.

P723 is produced by crossing the proprietary corn inbred line Qx47 with the proprietary corn synthetic P39B. Either parent may be used as the female parent or the male parent. P723's parents have large, highly branched tassels.

Although P723's primary use would be as a pollinator in the TOPCROSS® Grain Production System with blends of early to medium maturing corn hybrid male sterile grain parents, it is also an acceptable parent to be crossed with other high oil pollinators to develop derived pollinators, for example by crossing to earlier or later pollinators for expanding the use of its genetics to wider maturity grain parents.

Comparison of P723 to Synthetic Hybrid LP56.1

LP56.1 is a synthetic hybrid described in Bergquist U.S. Pat. No. 5,850,031. As shown in Tables 1 and 2, the timing and duration of P723 flowering is very similar to LP56.1 and about 1 day earlier to flower than the commercially used pollinator P22.1.

TABLE 1

Average of 1998–1999 LP56.1 and P723 Flowering Observations on the Number of Days from Planting to 10%, 50% and 90% of the Plants Shedding Pollen. (1998: 21 locations; 1999: 28 locations; 2 replicates/location)

| Pollinator | 10% Shedding | 50% Shedding | 90% Shedding |
|---|---|---|---|
| LP56.1 | 62.8 | 65.1 | 67.3 |
| P723 | 62.6 | 64.9 | 67.1 |

TABLE 2

Average of 1998–1999 P22.1 and P723 Flowering Observations on the Number of Days from Planting to 10%, 50% and 90% of the Plants Shedding Pollen. (1998: 14 locations; 1999: 11 locations; 2 replicates/location)

| Pollinator | 10% Shedding | 50% Shedding | 90% Shedding |
|---|---|---|---|
| P22.1 | 67.3 | 69.7 | 72.2 |
| P723 | 66.3 | 68.7 | 70.9 |

When used as a pollinator, P723 produces kernels with comparable oil concentration to those produced using LP56.1 as the pollinator (see Example below). However, grain from P723 TC BLEND® Seed Products has substantially increased test weight in comparison to grain produced from LP56.1 (see Table 8). P723 may have improved plant vigor over LP56.1, as suggested by cold soil germination tests (see Table 3) and yield measurements on the pollinator plants themselves (see Table 4).

TABLE 3

1999 Field Emergence Observations, Williamsburg IA, With A Very Early Planting Date (March 31, 1999) Providing Cold Soil Conditions. (3 replicates)

| Pollinator | Emergence | Interval from 1st Plant to 10 Plants Emerged |
|---|---|---|
| LP56.1 | 40% | 10 days |
| P723 | 70% | 2 days |

TABLE 4

1998 Yield Trial Results, Pollinators per se, Grown in 2-row × 19 ft. Plots in Three Midwest Locations (3 replicates/location)

| Pollinator | Yield (bu/A) | Harvest Moisture (%) | Test Wt. (lbs/bu) |
|---|---|---|---|
| LP56.1 | 76 | 24.7 | 48.5 |
| P723 | 90 | 23.8 | 50.5 |

EXAMPLES OF USING P723 AS A POLLINATOR

Strip test trials were conducted by Holden's Foundation Seeds, L.L.C. in the summer of 1998 to compare the characteristics of grain produced from various hybrids rendered male sterile and pollinated by P723 (High Oil Corn Grain) with the characteristics of grain produced from the same hybrids in their fertile state and not pollinated by P723. As Table 5 shows, the average oil concentration of the High Oil Corn Grain was three percentage points higher on a dry basis than the average oil concentration of grain from the corresponding fertile hybrids. Grain moisture at harvest was 0.7 percentage points higher, test weight was 0.5 lb/bu lower, and protein was 0.2 percentage points higher in the High Oil Corn Grain compared to the grain from the corresponding fertile hybrids.

TABLE 5

1998 TOPCROSS ® Grain Production System Strip Test Results Using P723 as Pollinator Across a Range of Hybrid Grain Parents
Absolute Increase or Decrease Over the Mean Value for Grain Produced from the Self- and Sib-pollinated Grain Parents

| Grain Moisture at Harvest (%) | Test Weight (lb/bu) | Oil concentration (% at 0% moisture) | Protein Concentration (% at 0% moisture) |
|---|---|---|---|
| +0.7 | −0.5 | +3.0 | +0.2 |

Table 6 represents 1998 strip test data for two grain parent hybrids (LH198SDms×LH172) and (LH198SDms×LH185) pollinated by P723 at a number of locations. As Table 6 shows, the average level of oil in grain arising from LH198SDms×LH172 pollinated by P723 was 7.4%, and for (LH198SDms×LH185 pollinated with P723 was 6.9%.

TABLE 6

1998 Strip Test Data Using LH198SDms hybrids as the Grain Parents

| Grain Parent | Grain Yield bu/acre | Grain Moisture at Harvest % | Test Weight lb/bu | Oil | Protein | Starch |
|---|---|---|---|---|---|---|
| | | | | % at 0% moisture | | |
| LH198SDms × LH172 | 171 | 18.8 | 55.9 | 7.4 | 8.7 | 68.4 |
| Number of locations | 23 | 23 | 19 | 19 | 19 | 19 |
| LH198SDms × LH185 | 174 | 18.0 | 56.1 | 6.9 | 8.7 | 68.8 |
| Number of locations | 22 | 22 | 18 | 18 | 18 | 18 |

Table 7 represents 1998 strip test data for the grain parent hybrid (LH198SDms×LH185) pollinated by P723 compared to data for the fertile check (LH198×LH185) when pollinated by itself:

TABLE 7

1998 TOPCROSS ® Grain Production System Strip Test Data Averaged Over A Number of Locations

| | Grain Yield bu/acre | Grain Moisture at Harvest % | Test Weight lb/bu | Oil | Protein | Starch |
|---|---|---|---|---|---|---|
| | | | | % at 0% moisture | | |
| Grain Parent Fertile Check (GP) | 188 | 18.6 | 55.8 | 4.5 | 8.4 | 72.2 |
| High Oil Corn Grain | 187 | 19.2 | 55.0 | 7.3 | 8.3 | 68.8 |
| High Oil Corn Grain as % of GP | 99.5 | 103 | 98.6 | 162 | 98.8 | 95.3 |
| Number of locations | 7 | 7 | 7 | 6 | 6 | 6 |

Grain arising on the male sterile grain parent pollinated by P723 (High Oil Corn Grain) exhibited, on average, 7.3% oil at 0% moisture. Grain arising on the fertile check exhibited, on average, only 4.5% oil. The oil concentration in the High Oil Corn Grain produced using the P723 pollinator was thus 162% of that in the grain arising on the grain parent check when pollinated by itself. Similar results were observed across a range of grain parents in 1999 (see Table 8).

TABLE 8

1999 TOPCROSS ® Grain Production System Strip Test Results Using P723 and LP56.1 as Pollinators Across a Range of Hybrid Grain Parents
Absolute Increase or Decrease Over the Mean Value for Grain Produced from the Self- and Sib-pollinated Grain Parents

| Pollinator | Grain Moisture at Harvest (%) | Test Weight (lbs/bu) | Oil concentration (%) | Protein Concentration (%) |
|---|---|---|---|---|
| P723 | −0.1 | −0.2 | +2.8 | 0 |
| LP56.1 | +0.4 | −1.7 | +3.2 | −0.2 |

Table 9 presents data comparing the performance of TC BLEND® Seed Products using the same grain parent, LH198SDms×LH172, with LP56.1 versus P723. These data indicate that in side-by-side comparisons, the P723 blend is slightly higher yielding and produces grain with about the same high oil concentration (0.2 percentage points higher) but with higher test weight than the LP56.1 blend.

TABLE 9

1998 TOPCROSS® Grain Production System Strip Test Results for LP56.1 versus P723 Used in TC BLEND® Seed Products with LH198SDms × LH172.

| Seed Blend | Yield (bu/A) | Moisture (%) | Oil (%, db) | Test Wt. (lbs/bu) |
|---|---|---|---|---|
| LH198SDms × LH172 + LP56.1 | 168 | 18.7 | 7.4 | 53.3 |
| LH198SDms × LH172 + P723 | 170 | 20.3 | 7.6 | 54.5 |
| No. of Locations: | 5 | 5 | 5 | 5 |

Table 10 presents data comparing the performance of TC BLEND® Seed Products using the same grain parent, LH198SDms×LH185, with P22.1 versus P723. These data indicate that in side-by-side comparisons, the P723 blend is slightly higher yielding and produces grain with about the same high oil concentration but with higher test weight than the P22.1 blend.

TABLE 10

1998 TOPCROSS® Grain Production System Strip Test Results for P22.1 versus P723 Used in TC BLEND® Seed Products with LH198SDms × LH185.

| Seed Blend | Yield (bu/A) | Moisture (%) | Oil (%, db) | Test Wt. (lbs/bu) |
|---|---|---|---|---|
| LH19BSDms × LH185 + P22.1 | 164 | 17.7 | 6.9 | 54.9 |
| LH198SDms × LH185 + P723 | 174 | 17.4 | 7.0 | 55.8 |
| No. of Locations: | 17 | 17 | 12 | 13 |

Applicant has made available to the public without restriction a deposit of at least 2500 seeds of maize hybrid P723 with the American Type Culture Collection (ATCC), Rockville, Md. 20852, ATCC Deposit No. PTA-2975. The seed deposited with the ATCC was taken from the same deposit maintained by Holden's Foundation Seeds, L.L.C, 503 S. Maplewood Ave., P. O. Box 839, Williamsburg, Iowa 52361 since prior to the filing date of this application. The deposit will be maintaind in the ATCC depository, which is a public depository, for a period of 30 years, or 5 years after the most recent request, or for the enforceable life of the patent, whicheveris longer, and will be replaced if it becomes nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A synthetic hybrid corn line designated P723, for which a representative sample of seeds has been deposited under ATCC Accession No. PTA-2975.

2. A hybrid corn seed designated P723, a representative sample of which has been deposited with the ATCC under Accession No. PTA-2975.

3. A hybrid corn plant produced by the seed of claim 2.

4. Pollen of the hybrid corn plant of claim 3.

5. A tissue culture comprising regenerable cells of the hybrid corn plant of claim 3.

6. A corn plant regenerated from regenerable cells of the tissue culture of claim 5.

7. A corn plant having substantially all the morphological and physiological characteristics of the hybrid corn plant of claim 3.

8. A corn plant having all the phenotypic, genotypic and physiological characteristics of the hybrid corn plant of claim 3.

9. A method for producing a hybrid corn seed designated P723 and having ATCC Accession No. PTA-2975, comprising the steps of:

a) planting in pollinating proximity seeds of corn lines Qx47, ATCC Accession No. PTA-2973, and P39B, ATCC Accession No. 97697;

b) cultivating corn plants resulting from the planting until the time of flowering;

c) emasculating the flowers of the plants of either inbred line Qx47 or P39B;

d) allowing cross pollination to occur between the inbred lines; and e) harvesting seeds produced on the emasculated plants.

10. Grain produced by crossing a hybrid corn plant according to claim 3 with another, different corn plant.

11. Seed produced by crossing a hybrid corn plant according to claim 3 with another, different corn plant.

12. A seed corn blend comprising a mixture of male sterile hybrid corn seed and the hybrid corn seed of claim 2.

13. Corn grain produced by the process of:

(a) planting, in pollinating proximity, the hybrid corn seed of claim 2 and seeds of a male sterile corn hybrid;

(b) cultivating corn plants resulting from the planting;

(c) allowing the P723 corn plants to pollinate the male sterile hybrid corn plants; and (d) harvesting the resulting corn grain from all plants.

14. A corn plant produced from a seed of claim 2 and having the ability to impart desirable grain quality traits to grain when used as a pollinator plant in the TOPCROSS® Grain Production System.

15. A corn plant produced from a seed of claim 2 having the ability to impart a high oil level to grain when used as a pollinator plant in the TOPCROSS® Grain Production System.

16. A corn plant derived from a seed of claim 2 and retaining the ability to impart a high oil level to grain when used as a pollinator in the TOPCROSS® Grain Production System.

* * * * *